United States Patent [19]

Höhl

[11] Patent Number: 5,529,911

[45] Date of Patent: Jun. 25, 1996

[54] PREPARATION OF GRANULES CONTAINING SALINOMYCIN

[75] Inventor: Rolf Höhl, Hofheim am Taunus, Germany

[73] Assignee: Hoechst Aktiengesellschaft, Frankfurt am Main, Germany

[21] Appl. No.: 293,163

[22] Filed: Aug. 19, 1994

Related U.S. Application Data

[63] Continuation of Ser. No. 156,923, Nov. 24, 1993, abandoned, which is a continuation of Ser. No. 805,900, Dec. 12, 1991, abandoned.

[30] Foreign Application Priority Data

Dec. 21, 1990 [DE] Germany .................. 40 41 190.7

[51] Int. Cl.$^6$ .................. C12P 17/16; C12P 17/18; C12P 17/02
[52] U.S. Cl. .................. 435/118; 426/807; 435/119; 435/123; 435/804
[58] Field of Search .................. 435/174, 187, 435/261, 804, 118, 119, 123; 426/807

[56] References Cited

U.S. PATENT DOCUMENTS

| | | | |
|---|---|---|---|
| 4,233,405 | 11/1980 | Neubeck | 435/187 |
| 4,395,491 | 7/1983 | Hohl et al. | 435/262 |
| 4,824,829 | 4/1989 | Klothen | 514/460 X |
| 4,876,198 | 10/1989 | Markussen | 435/187 X |

FOREIGN PATENT DOCUMENTS 0035125  9/1981  European Pat. Off. .

*Primary Examiner*—David M. Naff
*Attorney, Agent, or Firm*—Finnegan, Henderson, Farabow, Garrett & Dunner

[57] ABSTRACT

Granules containing salinomycin are prepared that are free-flowing, dust-free, and have unrestricted bioavailability of salinomycin. The granules are produced by fermenting a culture broth with a salinomycin producing microorganism to a residual fat content of about 24 to 30% by dry weight broth, adding to the fermented broth a cellulose ether and an anticaking agent, and spray drying the broth while adding a flow auxiliary to produce granules containing 10 to 26% by weight salinomycin. The granules also contain, based on the weight of the broth being fermented, 30 to 40% anticaking agent and flow auxiliary in a ratio of 3:1 to 9:1 and 0.5 to 2% cellulose ether. The anticaking agent is preferably a calcium carbonate such as chalk or a silica of natural origin such as diatomaceous earth, talc, or kaolin. The flow auxiliary is preferably a synthetic or precipitated silica.

18 Claims, No Drawings

PREPARATION OF GRANULES CONTAINING SALINOMYCIN

This application is a continuation, of application Ser. No. 08/156,923 filed Nov. 24, 1993, now abandoned; which is a continuation of application Ser. No. 07/805,900 filed Dec. 12, 1991, abandoned.

Processes for working up salinomycin culture broths are known (EP 0 035 125). In this process, a biomass spray-dried powder is produced from the solids in the salinomycin culture broth and subsequently 6% by weight (6% by weight salinomycin content), but not dust-free, pellets are produced with carrier material. The toxicological and occupational hygiene objections arising from this mean that there is a need for a way to produce a dust-free and abrasion-resistant, as well as free-flowing, agglomerate (or microgranules) which ought, besides a defined particle size, to have good admixture properties with animal feedstuffs and whose bioavailability of active substance ought to be unrestricted. At the same time, the intention was to produce high percentage granules.

An agglomerate granule produced by the process of EPO 035 125 or by the known FSD (fluid stage drying) process readily disintegrates and forms dust when the residual extract content (residual fat content 3.5% by weight=17.5% by weight in the dry matter of the culture broth) of the culture broth is maximally diminished.

If the known way of subsequent granulation with compression and milling had been followed, it would have required considerable investment, and the product would have become correspondingly costly. In addition, an experimental product produced in this way still does not have all the required properties, because the quality requirements are in some cases contradictory. It is known that a product which flows well produces dust but a dust-free product cakes. In addition, an abrasion-resistant product has only limited bioavailability.

The invention relates to salinomycin biomass granules which are free-flowing and dust-free, retain this freedom from dust during further processing even when abrasive forces occur, and whose bioavailability of active substance is unrestricted.

The granules contain according to the invention 30 to 40% by weight of anticaking agent and flow auxiliaries and 0.5—2% by weight of cellulose ethers based on the weight of the culture broth produced in the fermentation, where the ratio of anticaking agent to flow auxiliary is 3:1 to 9:1.

The invention also relates to a process for the production of salinomycin biomass granules by spray drying a salinomycin culture broth, which comprises adding anticaking agent and cellulose ethers to the culture broth before the spray drying, and adding the flow auxiliary during the spray drying.

The process according to the invention produces in one step 10–26% by weight, preferably 10 to 15% by weight, salinomycin biomass granules.

Whereas a residual fat content which is lower than 3.5% is aimed at for the spray-dried powder according to EPO 035 125, a residual fat content of 5–6%, preferably 5–5.6%, in the culture broth (about 24–30%, preferably 25–27%, based on the dry matter) proves to be optimal for the granule process according to the invention.

Thus the diminution in the residual fat content is not carried out to the maximum extent but is discontinued at a higher level which is optimal for the abovementioned aims.

Depending on the salinomycin content of the culture broth, 30–40% by weight of inert material (anticaking agent and flow auxiliary) are added. The anticaking agents: flow auxiliary ratio is 3:1 to 9:1, preferably 7:1. Of these, the anticaking agent is stirred into the culture broth. The remainder of the inert material (=flow auxiliary) is blown into the spray tower during drying.

Examples of anticaking agents which are used are finely divided calcium carbonates and silicas of natural origin, for example chalk, diatomaceous earth, talc or kaolin, and of flow auxiliaries are synthetic silicas or precipitated silica, it being possible to employ the anticaking agents both alone and in mixtures with one another.

It is possible by increasing the amount of flow auxiliary to improve the flow properties significantly, although there is then also an increase in the dust number, especially when abrasive forces occur in further processing of the product.

This can be counteracted by not continuing the diminution in the residual fat content of the culture broth to the maximum levels but discontinuing at higher levels. In this case the product does not dust and shows no abrasion, but it again sticks and cakes.

Addition of oil to bind the dust is no use for the same reasons.

It is known that granules can be externally hardened by spraying on cellulose ethers, for example carboxymethylcellulose (CMC) or similar substances. However, this has an adverse effect on the bioavailability of the active substance. It is likewise known that CMC, stirred into an oily aqueous suspension, produces a very fine dispersion of the oil droplets, which further increases the dust formation after spray drying.

It has now been found, surprisingly, that addition of CMC to the culture broth before the spray drying results in a product which has satisfactory bioavailability without the granulation in the spray drier being hindered by the fine dispersion of the oil (and salinomycin) droplets in the culture broth. 0.5–2% by weight, based on the culture broth, preferably 1% by weight are employed. The resulting granules are also internally hardened by CMC and are no longer prone to dust formation even if abrasive forces occur. The resulting granules are free-flowing and have a Jenike flow factor of at least 10.

The following particle size spectrum is achieved by technical parameters of the drying system: >2.000 mm, 0.0–0.5%, preferably 0% 1.000–2.000 mm, 0.0–1.0%, preferably 0% 0.500–1.000 mm, 0.5–5%, preferably less than 5% 0.180–0.500 mm, 50–80%, preferably 70% 0.100–1.180 mm, 10–20%, preferably 20% <0.100 mm, 0–10%, preferably less than 5%.

The following examples are intended to illustrate the invention. Unless otherwise indicated, % data mean percentages by weight.

It is possible and advantageous to use a spray drier which has integrated fluidized bed and which operates by the FSD process (FSD drier supplied by Niro Atomizer, Copenhagen, Denmark) to produce the granules.

EXAMPLE I

Salinomycin culture broth is fermented in a known manner so that a dry matter content of about 20% is present at the end of the fermentation. During the fermentation the addition of oil is controlled in such a way that the extractable residual fat content in the drymatter of the finished culture broth is 24–30%.

After this the pH is adjusted to pH 10 with NaOH and the culture broth is heated at 80° C. for 2 hours. This completely kills the producer strain.

Subsequently, 1% by weight of carboxymethylcellulose (based on the amount of culture broth) is stirred into the culture broth. The culture broth treated in this way is preferably pumped via a colloid mill into the vigorously stirred receiver of the spray drying system.

In the meantime, the salinomycin content and the dry matter of the culture broth, and the residual fat content in the dry matter, are determined. When the residual fat content is 24–25% in the dry matter of the culture broth, it is calculated how much anticaking agent in the form of chalk must be stirred into the drier receiver to obtain a salinomycin content of 13% in the spray-dried powder. In this case, 30% anticaking agent, based on the amount of culture broth, are added. The pumpability of the broth remains good and it is pumped to the nozzles or the disk of an FSD spray drier. The broth is sprayed in at the top of the drier at a drying temperature of about 200°–240° C. The drying gas with less than 8% oxygen leaves the drier, loaded with water, at a temperature of about 90° C. The spray-dried powder, which is not yet completely dry, falls onto the fluidized bed which is integrated into the drier cone and is finally dried there with drying gas heated to about 85° C.

The fines in the spray-dried powder are carried out with the drying gas, separated out in cyclones (apparatus for separating fine-particle mixtures according to particle size) and returned via a shaking channel to the integrated fluidized bed.

Into this returning product stream sufficient silica (4%) (flow auxiliary) is metered for the salinomycin content of the product to be 12% as exactly as possible. During the final drying on the integrated fluidized bed, the flow auxiliary takes part in the formation of the granules so that a free-flowing (flow factor >10) non-dusting, abrasion-resistant product which is not prone to caking and has good bioavailability of the active substance is obtained. About 70% of the resulting product has a particle size between 0.180 and 0.500 mm.

EXAMPLE II

The fermentation and the subsequent treatment of the culture broth is carried out as described in Example I, including the addition of carboxymethylcellulose.

The laboratory analysis shows a residual fat content of 30% in the drymatter of the culture broth. The addition of anticaking agent (chalk) into the drier receiver is reduced. It is calculated so that the salinomycin content of the spray-dried powder would still be 14%. On the other hand, the addition of flow auxiliary (silica) to the fluidized bed is increased so that a final content of 12% salinomycin is obtained as exactly as possible (26% anticaking agent, 8% flow auxiliarybased on the culture broth). Retaining the other drying conditions results, despite the less favorable residual fat content of the culture broth, in free-flowing (flow factor >10), non-caking, dust-free granules of the required particle size and with good bioavailability of the active substance.

EXAMPLE III

The working up of the culture broth is carried out as described in Example II using a vacuum thin-film evaporator. Only as much of the anticaking agent (chalk) calculated in Example I is stirred into the concentrate for the broth to remain pumpable and sprayable. The addition of flow auxiliary (Aerosil®, Sipernat®) onto the fluidized bed of the FSD spray drier is increased so that pellets with a salinomycin content of 12% as exactly as possible and the other properties described in Example I are obtained.

EXAMPLE IV

The culture broth is worked up as described in Examples I to III. The physical properties are immediately tested in the laboratory. If the flow properties are not satisfactory, the amount of silica (flow auxiliary) is increased while, at the same time, reducing the addition of anticaking agent (chalk). If the freedom from dust is insufficient, conversely the amount of chalk is increased and the amount of silica is reduced. However, the total of inert material is calculated so that the required salinomycin content in the granules is obtained.

I claim:

1. A process for the production of granules containing salinomycin which comprises the steps of:
   (a) fermenting a culture broth containing salinomycin producing microorganisms wherein said culture broth is fermented to a residual fat content of about 24 to 30% by weight based on dry matter of the broth;
   (b) adding to the culture broth a cellulose ether and an anticaking agent selected from the group consisting of finely divided calcium carbonates and silicas of natural origin; and
   (c) spray drying the culture broth while adding a flow auxiliary thereto,
   wherein said flow auxiliary is selected from the group consisting of synthetic silica and precipitated silica, to produce granules comprising 10 to 26% salinomycin by weight; and
   further comprising the following ingredients in percent based on the weight of the culture broth in which said salinomycin producing microorganisms have been fermented:
   (1) 30 to 40% of an anticaking agent and a flow auxiliary, wherein the ratio of anticaking agent to flow auxiliary is 3:1 to 9:1; and
   (2) 0.5 to 2% of a cellulose ether.

2. The process as claimed in claim 1, wherein the spray drying is conducted in a spray tower and the flow auxiliary is metered into a fluidized bed zone in the spray tower.

3. The process as claimed in claim 1, wherein chalk is employed as anticaking agent and silica is employed as flow auxiliary.

4. The process as claimed in claim 1 wherein said residual fat content is 25 to 27%.

5. The process as claimed in claim 1 wherein said cellulose ether is carboxymethylcellulose.

6. The process as claimed in claim 1 wherein said calcium carbonate is chalk.

7. The process as claimed in claim 1 wherein said silica of natural origin is diatomaceous earth.

8. The process as claimed in claim 1 wherein said silica of natural origin is talc.

9. The process as claimed in claim 1 wherein said silica of natural origin is kaolin.

10. Granules containing salinomycin, wherein said granules are produced by the process of claim 11.

11. Granules containing salinomycin as claimed in claim 10, wherein the granules have a salinomycin content of 10 to 15% by weight.

12. Granules containing salinomycin as claimed in claim 10, wherein the granules have the following particle spectrum:

>2,000 mm, 0.0–0.5%,
1,000–2,000 mm, 0.0–1.0%,
0.500–1,000 mm, 0.5–5%,
0.180–0.500 mm, 50–80%,
0.100–1.180 mm, 10–20%,
<0.100 mm, 0–10%.

13. Granules containing salinomycin, wherein said granules are produced by the process of claim 4.

14. Granules containing salinomycin as claimed in claim 10, wherein the cellulose ether is carboxymethylcellulose.

15. Granules containing salinomycin as claimed in claim 10 wherein said calcium carbonate is chalk.

16. Granules containing salinomycin as claimed in claim 10 wherein said silica of natural origin is diatomaceous earth.

17. Granules containing salinomycin as claimed in claim 10 wherein said silica of natural origin is talc.

18. Granules containing salinomycin as claimed in claim 10 wherein said silica of natural origin is kaolin.

* * * * *

UNITED STATES PATENT AND TRADEMARK OFFICE
CERTIFICATE OF CORRECTION

PATENT NO. : 5,529,911
DATED : June 25, 1996
INVENTOR(S) : Rolf Höhl

It is certified that error appears in the above-indentified patent and that said Letters Patent is hereby corrected as shown below:

Claim 12, Column 5, Line 1, "2,000" should read --2.000--;

Claim 12, Column 5, Line 2, "1,000-2,000" should read --1.000 - 2.000--;

Claim 12, Column 5, Line 3, "1,000" should read --1.000--.

Signed and Sealed this

Twenty-eighth Day of January, 1997

Attest:

BRUCE LEHMAN

*Attesting Officer*  *Commissioner of Patents and Trademarks*